United States Patent
Siochi

[19]
[11] Patent Number: 6,128,366
[45] Date of Patent: Oct. 3, 2000

[54] DOSIMETRY ERROR REDUCTION FOR OPTIMIZED STATIC INTENSITY MODULATION

[75] Inventor: Ramon Alfredo Siochi, Fairfield, Calif.

[73] Assignee: Siemens Medical Systems, Inc., Iselin, N.J.

[21] Appl. No.: 09/112,073

[22] Filed: Jul. 8, 1998

[51] Int. Cl.[7] .................................................. A61N 5/10

[52] U.S. Cl. ............................................. 378/65; 378/901

[58] Field of Search .................................. 378/64, 65, 901

[56] References Cited

U.S. PATENT DOCUMENTS

| | | | |
|---|---|---|---|
| 5,602,892 | 2/1997 | Llacer | 378/65 |
| 5,663,999 | 9/1997 | Siochi | 378/65 |
| 5,859,891 | 1/1999 | Hibbard | 378/62 |

Primary Examiner—David V. Bruce

[57] ABSTRACT

A radiation therapy delivery and dosimetry error correction system. Rather than iteratively creating more segments to correct for dosimetry errors, the present invention receives the outputs from a segment optimization algorithm (i.e., a set of segments and an initial set of monitor units) and varies the number of monitor units associated with each segment to correct for dosimetry errors. Only if an extreme case exists will additional segments be added.

18 Claims, 4 Drawing Sheets

DOSIMETRY ERROR REDUCTION FOR OPTIMIZED STATIC INTENSITY MODULATION

BACKGROUND OF THE INVENTION

The present invention relates to a radiation emitting device, and more particularly, to a system and method for efficiently delivering radiation treatment.

DESCRIPTION OF THE RELATED ART

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located in the gantry for generating a high energy radiation beam for therapy. This high energy radiation beam can be an electron beam or photon (X-ray) beam. During treatment, this radiation beam is trained on one zone of a patient lying in the isocenter of the gantry rotation.

To control the radiation emitted toward an object, a beam shielding device, such as a plate arrangement or a collimator, is typically provided in the trajectory of the radiation beam between the radiation source and the object. An example of a plate arrangement is a set of four plates that can be used to define an opening for the radiation beam. A collimator is a beam shielding device which could include multiple leaves, for example, a plurality of relatively thin plates or rods, typically arranged as opposing leaf pairs. The plates themselves are formed of a relatively dense and radiation impervious material and are generally independently positionable to delimit the radiation beam.

The beam shielding device defines a field on the object to which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the organs surrounding and overlying the tumor determines the dosage that can be delivered to the tumor.

The delivery of radiation by a radiation therapy device is prescribed and approved by an oncologist. The prescription is a definition of, for example, a particular volume and the level of radiation permitted to be delivered to that volume. Actual operation of the radiation equipment, however, is normally done by a therapist. When the therapist administers the actual delivery of the radiation treatment as prescribed by the oncologist, the radiation-emitting device is programmed to deliver that specific treatment. When programming the treatment, the therapist has to take into account the actual radiation output and has to adjust the dose delivery based on the plate arrangement opening to achieve the prescribed radiation treatment at the desired depth in the target.

A known system for determining an efficient process for radiation treatment is described in U.S. Pat. No. 5,663,999, assigned to Siemens Medical Systems, Inc. The system described in U.S. Pat. No. 5,663,999 defines a field on an object for irradiation. The field is divided into multiple segments. Each of the segments has defined parameters. More particularly, each of the segments is individually treated with radiation by defining an opening between the radiation source and the object and by generating a radiation beam. The opening is placed over one of the segments. This opening is capable of delimiting the radiation beam to the defined parameters of that segment. This treatment is done for each of the segments until the field is irradiated.

In such radiation treatment methods, dosimetry errors may be created by transmission through the leaves of the collimator and scattered radiation. If an iterative system is employed for dosimetry correction, the result tends to be the creation of more segments. This can result in undesirable delays in delivering treatment. Accordingly, there is a need for an improved dosimetry error correction method.

SUMMARY OF THE INVENTION

These problems in the prior art are overcome in large part by a system and method for radiation therapy delivery and dosimetry error correction according to the present invention. More particularly, rather than iteratively creating more segments to correct for dosimetry errors, the present invention receives the outputs from a segment optimization algorithm (i.e., a set of segments and an initial set of monitor units) and varies the number of monitor units associated with each segment to correct for dosimetry errors. Only if an extreme case exists will additional segments be added.

BRIEF DESCRIPTION OF THE DRAWINGS

A better understanding of the present invention can be obtained when the following detailed description is considered in conjunction with the following drawings in which.

DETAILED DESCRIPTION OF THE INVENTION

Figure 1:
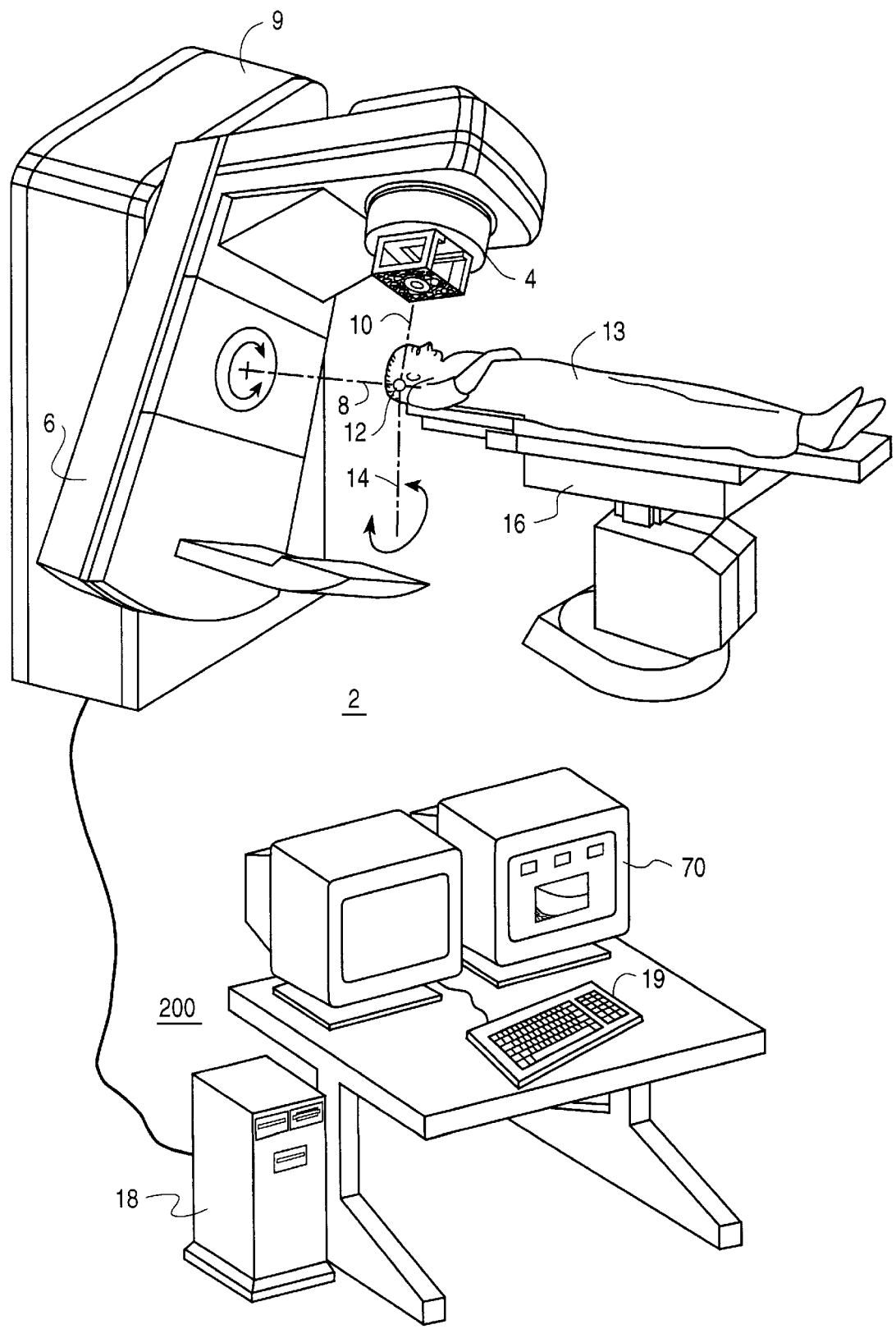
FIG. 1 is a diagram of a radiation treatment device and treatment console according to an embodiment of the present invention.

Referring to the drawings and especially to FIG. 1, a radiation treatment apparatus embodying the present invention is shown therein and generally identified by reference numeral 2. The radiation treatment apparatus 2 includes a beam shielding device (not shown) within a treatment head 4, a control unit in a housing 9 and a treatment unit 200 according to the present invention. The radiation treatment device 2 includes a gantry 6 which can be swiveled around a horizontal axis of rotation 8 in the course of a therapeutic treatment. The treatment head 4 is fastened to projection of the gantry 6. A linear accelerator is located in the gantry 6 to generate the high powered radiation required for the therapy. The axis of the radiation bundle emitted from the linear accelerator and the gantry 6 is designated by 10. Electron, photon or any other detectable radiation can be used for the therapy.

During the treatment, the radiation beam is trained on a zone 12 of an object 13, for example, a patient who is to be treated and who lies at the isocenter of the gantry rotation. The rotational axis 8 of the gantry 6, the rotational axis 14 of a treatment table 16, and the beam axis 10 intersect in the isocenter.

The plates or leaves of the beam shielding device within the treatment head 4 are substantially impervious to the emitted radiation. The collimator leaves or plates are mounted between the radiation source and the patient in order to delimit the field. Areas of the body, for example, healthy tissue, are therefore subject to as little radiation as possible and preferably to none at all. The plates or leaves are movable such that the distribution of radiation over the field need not be uniform (one region can be given a higher dose than another). Furthermore, the gantry can be rotated so as to allow different beam angles and radiation distributions without having to move the patient.

The radiation treatment device 2 also includes a central treatment processing or control unit 200 which is typically located apart from the radiation treatment device 2. The radiation treatment device 2 is normally located in a different room to protect the therapist from radiation. The treatment unit 200 includes output devices such as at least one visual display unit or monitor 70 and an input device such as a keyboard 19. Data can be input also through data carriers such as data storage devices or a verification and recording or automatic setup system.

The treatment processing unit 200 is typically operated by the therapist who administers actual delivery of radiation treatment as prescribed by an oncologist by using the keyboard 19 or other input device. The therapist enters into the control unit of the treatment unit 200 the data that defines the radiation dose to be delivered to the patient, for example, according to the prescription of the oncologist. The program can also be input via another input device, such as a data storage device. Various data can be displayed before and during the treatment on the screen of the monitor 70.

Figure 2:
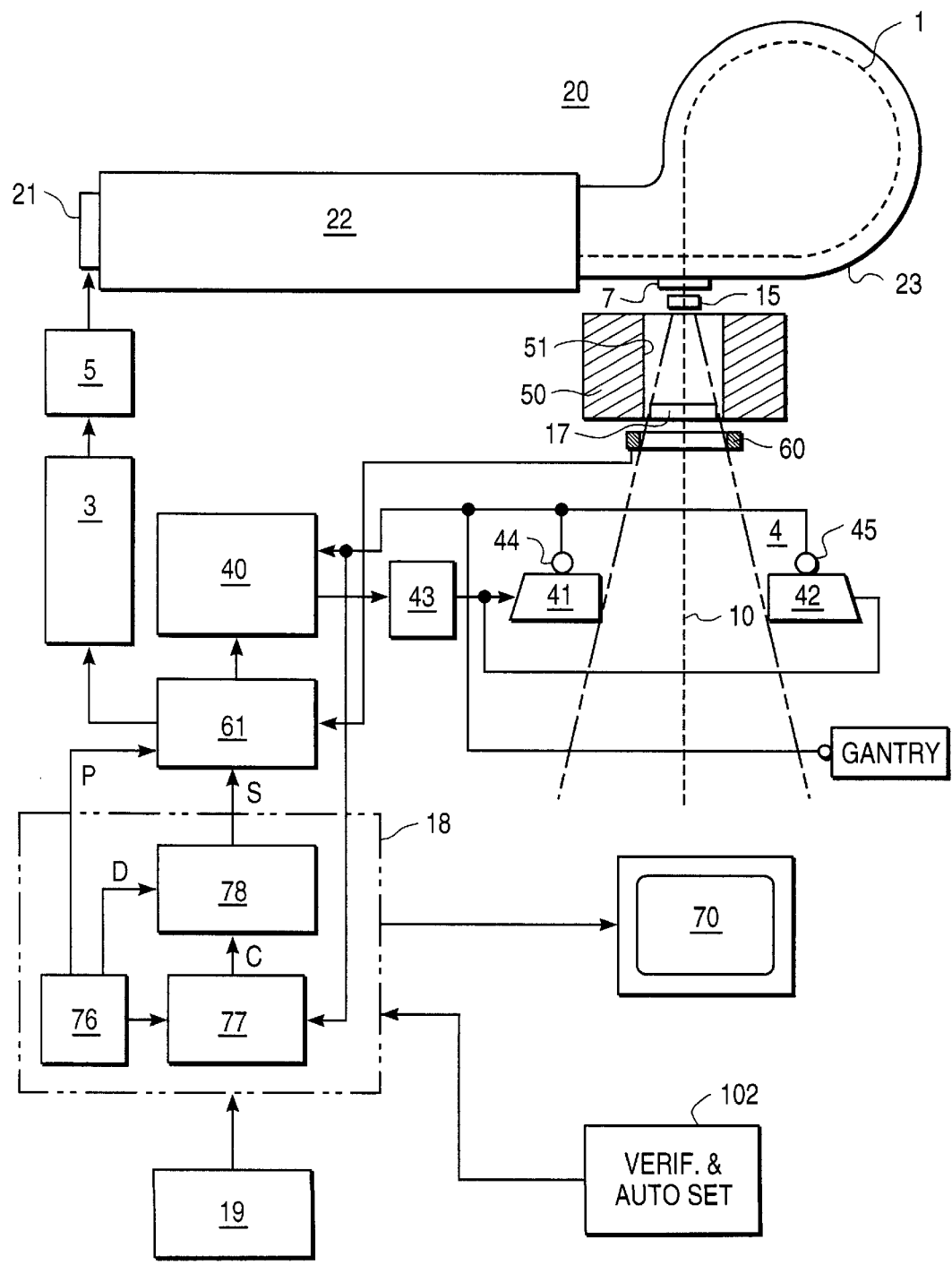
FIG. 2 is a more detailed block diagram illustrating portions of the present invention.

Turning now to FIG. 2, a block diagram of the radiation treatment device 2 and portions of the treatment unit 200 are illustrated in greater detail. An electron beam 1 is generated in an electron accelerator 20. The electron accelerator 20 includes an electron gun 21, a wave guide 22 and an evacuated envelope or guide magnet 23. A trigger system 3 generates injector trigger signals and supplies them to the injector 5. Based on these injector trigger signals, the injector 5 generates injector pulses which are fed to the electron gun 21 in the accelerator 20 for generating electron beam 1. The electron beam 1 is accelerated and guided by the wave guide 22. For this purpose, a high frequency source (not shown) is provided, which supplies radio frequency signals for the generation of an electromagnetic field supplied to the wave guide 22. The electrons injected by the injector 5 and emitted by the electron gun 21 are accelerated by this electromagnetic field in the wave guide 22 and exit at the end opposite to electron gun 21 in electron beam 1. The electron beam 1 then enters a guide magnet 23 and from there is guided through a window 7 along axis 10. After passing through a first scattering foil 15, the beam goes through a passageway 51 of a shield block 50 and encounters a flattening filter 17. Next, it is sent through a measuring chamber 60 in which the dose is ascertained. If the scattering foil is replaced by a target, the radiation beam is an X-ray beam; in this case, the flattening filter 17 may be absent, but it is typically present.

Finally, a beam shielding device 401 is provided in the path of radiation beam 1, by which the irradiated field of the subject of investigation is determined. As illustrated, the beam shielding device 401 includes a plurality of opposing plates 41 and 42, only two of which are illustrated for convenience. In one embodiment, additional pairs of plates (not shown) are arranged perpendicular to plates 41 and 42. The plates 41, 42 are moved with respect to axis 10 by a drive unit 43 (which is indicated in FIG. 2 only with respect to plate 41) to change the size of the irradiated field. The drive unit 43 includes an electric motor which is coupled to the plates 41 and 42 and which is controlled by a motor controller 40. Position sensors 44 and 45 are also coupled to the plates 41 and 42, respectively for sensing their positions. As discussed above, the plate arrangement 401 may alternatively include a multi-leaf collimator having many radiation blocking leaves.

Figure 3:
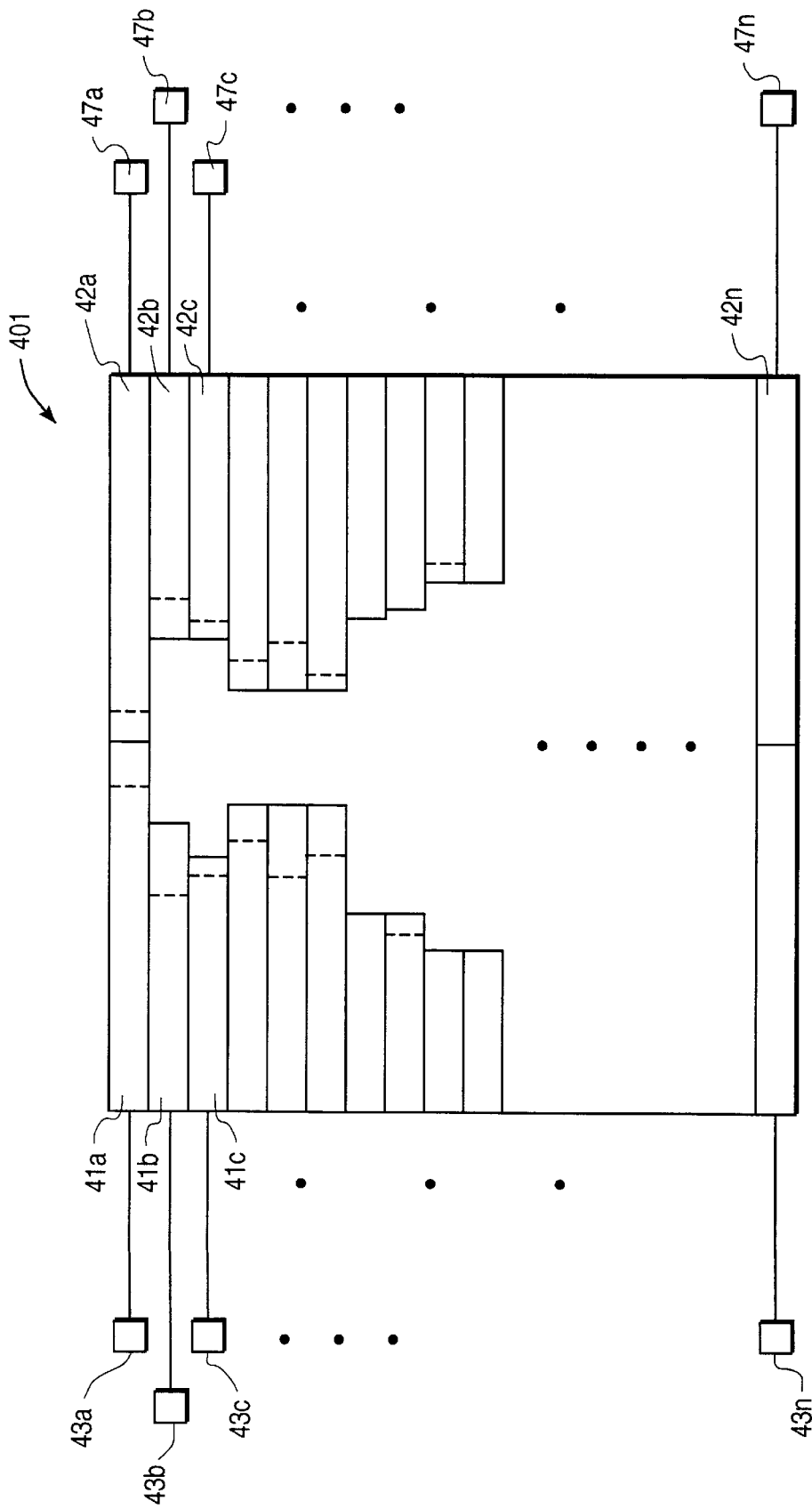
FIG. 3 is a diagram of a multi-leaf collimator according to an embodiment of the invention.

The leaves of such a multi-leaf collimator are illustrated in greater detail in FIG. 3. Opposing leaf, or rod pairs 41a–41n, 42a–42n, each include a motor or drive unit 43a–43n, and 47a–47n, respectively. The drive units drive the rods, or leaves, in and out of the treatment field, thus creating the desired field shape. The rods, or leaves, are relatively narrow, and cast a shadow of about 0.5 to 1. cm at isocenter.

Turning back to FIG. 2, the motor controller 40 is coupled to a dose unit 61 which includes a dosimetry controller and which is coupled to a central processing unit 18 for providing set values for the radiation beam for achieving given isodose curves. The output of the radiation beam is measured by a measuring chamber 60. In response to the deviation between the set values and the actual values, the dose control unit 61 supplies signals to a trigger system 3 which changes in a known manner the pulse repetition frequency so that the deviation between the set values and the actual values of the radiation beam output is minimized. In such a radiation device, the dose absorbed by the object 13 is dependent upon movement of the collimator leaves.

The central processing unit 18 is programmed by the therapist according to the instructions of the oncologist and performs optimization according to the present invention so that the radiation treatment device carries out the prescribed radiation treatment. The delivery of the radiation treatment is input through a keyboard 19. The central processing unit 18 is further coupled to a dose control unit 61 that generates the desired values of radiation for controlling trigger system 3. The trigger system 3 then adapts the pulse radiation frequency and other parameters in a corresponding, conventional manner. The central processing unit 18 further includes a control unit 76 which controls execution of the program and the opening and closing of the collimator plates 41, 42 according to the present invention to deliver radiation according to a desired intensity profile.

As discussed above, the present invention relates to varying the number of monitor units associated with each segment output from an intensity modulation optimization algorithm. One such optimization algorithm is described in U.S. Pat. No. 5,663,999, assigned to Siemens Medical Systems, Inc., which is herein incorporated by reference in its entirety as if fully set forth herein.

For the set of segments which make up the intensity modulated treatment, the experimental intensity produced at a location (r,c) in a matrix mapped onto the patient plane can be expressed as:

$$I_e(r,c) = \Sigma \beta_i s_i (S_i(r,c) + L\sigma_i(r,c) + \gamma_i(r,c)) \tag{1}$$

$S_i(r,c) = 1$ if (r,c) is not in primary beam
  0 if (r,c) is not in primary beam
$\sigma_i(r,c) = 1$ if (r,c) is not in primary beam and not under jaws for the ith segment
  0 if (r,c) is in primary beam or under jaws
$\gamma_i(r,c)$ = scatter contribution from segment i to the point (r,c)
L = % transmission through MLC leaf
$s_i$ = number of monitor units for the ith segment calculated by segmentation algorithm without considering errors $\beta_i$=dosimetry correction factor for the ith segment If I (r,c) is the desired intensity to be delivered, then an initial set of shape matrices $S_i$ and an initial set of Monitor Units $s_i$ can be determined using segmentation algorithms such as those described in the U.S. Pat. No. 5,663,999. However, the set of segments will not include scattering and transmission terms. Thus, an experimental intensity $I_e$ (r,c) is calculated with the dosimetry correction factors ($\beta_i$) initially set to 1. The experimental intensity $I_e$ (r,c) and the desired intensity values I (r,c) are then used to calculate an error matrix E (r,c) using Equation 2 below:

$$E(r, c) = \frac{|I(r, c) - I_e(r, c)|}{I(r, c)} \quad (2)$$

For each segment, an average error may be determined using Equation 3:

$$Ea_i = \frac{\sum_r \sum_c S_i(r, c) E(r, c)}{\sum_r \sum_c S_i(r, c)} \quad (3)$$

As can be appreciated, the segment having the maximum average error is the segment that contributes the most to the error. The value of $\beta_i$ for this segment is varied to try to "zero out" the largest error in this segment. If the error matrix for the ith segment is defined in Equation 4 below, then the new value of $\beta_i$ is defined in Equation 5:

$$E_i(r, c) = \frac{S_i(r, c)(I(r, c) - I_e(r, c))}{s_i} \quad (4)$$

$$\beta new_i = \beta old_i + \text{SignMaxAbs}(E_i(r, c)) * \text{Avg}(|E_i(r, c)|)$$

where the SignMaxAbs function takes the sign (+ or −) of the segment error matrix entry whose absolute value is the maximum for the matrix, and the Avg function takes the average of the absolute values of the entries in the segment error matrix. This adjustment for the scaling factor is only done for the factor which corresponds to the segment with the maximum average error. One can, alternatively, rank the segments in order of decreasing average error and change all the correction factors in that order. This forces all the correction factors to be changed the same number of times (e.g., if there are three segments and the first segment has the maximum value, then after changing that, only the second and third segments should be considered as candidates for change. If the third segment has a higher maximum error, then the third correction factor is changed. Finally, the second correction factor is changed. At this point, the next iteration can use all three segments again in the determination of which correction factor to change). This forces the algorithm to look at other segments that could affect the error reduction.

Once this adjustment to the scaling factor is made, the experimental intensity matrix is calculated again and the error process is repeated, i.e., the segment with the maximum average error is again determined and the dosimetry correction factor for that segment is again adjusted. The process stops once all the values in the error matrix are below some specified minimum or the values do not decrease after some specified number of iterations. If the values do not decrease after some smaller number of iterations, a re-normalization can be performed where all the correction factors are divided by the weighted average value of the correction factors. After several more iterations beyond this, if the error does not decrease, then the process stops. At that point, the final values of the dosimetry correction factors have been determined, and the treatment may proceed.

However, if it is impossible to meet some specified error criterion, a "partial segment boost" may be provided. This may occur, for example, when one segment contains multiple regions with different scattering properties. In particular, for example, a "teardrop" shaped segment may have different scattering properties at different ends of the "teardrop." The regions which receive a lot of scattering (for example, the larger end of the teardrop) are covered with the jaws and additional monitor units are delivered to the regions which receive little scattering (for example, the smaller end of the teardrop).

This process keeps the total number of segments, and hence, the treatment time to a minimum by trying to avoid the creation of new segments. It is noted that the process of adjusting parameters to minimize the error can be accomplished through other well known numerical procedures such as least squares and gradient methods. The initial segmentation routine may also be modified such that the set of segments lends itself to this error minimization process, for example, by using closing window techniques instead of curtain shutter techniques, such as described in Svenson, et al., "An Analytical Solution for the Dynamic Control of Multileaf Collimators," PHYS. MED. BIOL., 39:3761, (1994), which is hereby incorporated by reference in its entirety as if fully set forth herein.

Figure 4:
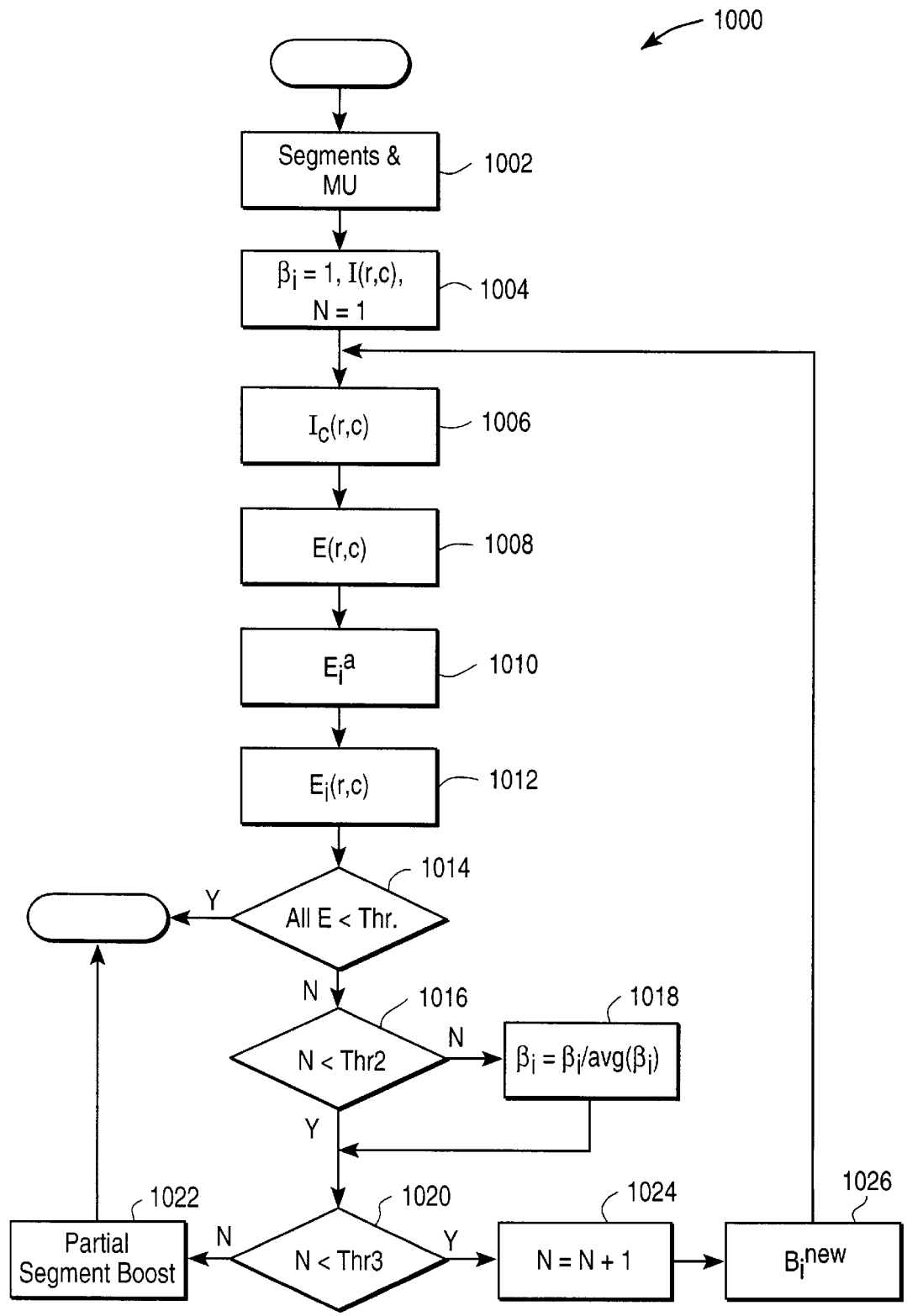
FIG. 4 is a flowchart illustrating a method according to an embodiment of the present invention.

Turning now to FIG. 4, a flowchart 1000 illustrating operation of an embodiment of the invention is shown. In particular, in a step 1002, an initial set of segments and monitor units is determined. This determination may be made using, for example, the system described in U.S. Pat. No. 5,663,999. In a step 1004, the initial dosimetry correction factors $\beta_i$ for the ith segment, and an index value N, are set to unity. The index value is used to count the number of iterations used. A set of experimental intensity values $I_e$ based on the dosimetry correction factors are calculated in a step 1006, using Equation 1. In a step 1008, an error matrix E (r,c) is calculated using Equation 2. In a step 1010, an average error for each segment is determined using Equation 3. In a step 1012, an error Ei matrix for the ith segment is calculated using Equation 4. In a step 1014, it is determined whether the error matrices for the ith segments are below a predetermined threshold. If they are, then the system stops and the final values for the correction factors are used.

However, if the average errors for the ith segment are not all below the predetermined threshold, then the index value N is checked to see if it is still below a predetermined threshold, in a step 1016. If not, then in a step 1018, the dosimetry correction factors are renormalized by dividing each correction factor by the weighted average of the correction factors; the applied weights are the corresponding original numbers of monitor units $s_i$. Next, the index value N is checked against a next threshold in a step 1020, and if less than this threshold, is incremented in a step 1024. Next, a new dosimetry correction factor is calculated for the segment which corresponds to the segment with the maximum average error using Equation 5. Next the new $\beta_i$ are used as the system cycles to step 1006.

If, in step 1020, the index value N had exceeded the threshold, then the system assumes that a partial segment boost is needed, which is applied in step 1022.

What is claimed is:

1. A method for dosimetry correction in a radiation therapy device, comprising:
   identifying an initial set of segments for radiation delivery, including identifying a number of monitor units for each of said segments;
   determining an error for each of said segments;
   determining a plurality of correction factors related to each of said segments;
   adjusting a correction factor for a segment identified as having a maximum error; and
   repeating said determining and adjusting steps until said error matches a predetermined condition.

2. A method according to claim 1, wherein said predetermined condition is an error threshold.

3. A method according to claim 1, wherein said predetermined condition is a failure to decrease after a predetermined number of iterations.

4. A method according to claim 1, including adjusting one or more of said segments if said predetermined condition is not met.

5. A method according to claim 1, wherein said determining said error includes using the following equations:

$$I_e(r,c) = \Sigma \beta_i s_i(S_i(r,c) + L\sigma_i(r,c) + \gamma_i(r,c))$$

$$S_i(r,c) = \begin{cases} 1 & \text{if } (r,c) \text{ is in primary beam} \\ 0 & \text{if } (r,c) \text{ is not in primary beam} \end{cases}$$

$$\sigma_i(r,c) = \begin{cases} 1 & \text{if } (r,c) \text{ is not in primary beam and not under jaws for the } i\text{th segment} \\ 0 & \text{if } (r,c) \text{ is in primary beam or under jaws} \end{cases}$$

$\gamma_i(r,c)$ = scatter contribution from segment i to the point (r,c)
L = % transmission through MLC leaf
$s_i$ = number of monitor units for the ith segment calculated by segmentation algorithm without considering errors
$\beta_i$ = dosimetry correction factor for the ith segment $$E(r,c) = \frac{|I(r,c) - I_e(r,c)|}{I(r,c)}$$

$$Ea_i = \frac{\sum_r \sum_c S_i(r,c) E(r,c)}{\sum_r \sum_c S_i(r,c)}$$

where I is the experimental intensity, E (r,c) is an error matrix over all segments, and E is an average error for the segment.

6. A method according to claim 5, said determining a plurality of correction factors including setting said correction factors to one or more predetermined initial settings.

7. A method according to claim 6, said adjusting a plurality of correction factors including using the following equations:

$$E_i(r,c) = \frac{S_i(r,c)(I(r,c) - I_e(r,c))}{s_i}$$

$$\beta new_i = \beta old_i + \text{SignMaxAbs}(E_i(r,c)) * \text{Avg}(|E_i(r,c)|).$$

8. A method for dosimetry correction in a radiation therapy device, comprising:
   identifying a set of segments, each of said segments defined by a setting of one or more radiation shielding devices;
   identifying an associated set of monitor units for each of said segments;
   identifying dosimetry errors; and
   varying said associated monitor units for at least one of said segments to correct for said dosimetry errors without adjusting said settings of said one or more radiation shielding devices.

9. A method according to claim 5, further including varying a setting of said one or more radiation shielding devices if correction of said dosimetry errors by varying said monitor units fails to meet one or more predetermined criteria.

10. A system for dosimetry correction in a radiation therapy device, comprising:
    means for identifying an initial set of segments for radiation delivery, including identifying a number of monitor units for each of said segments;
    means for determining an error for each of said segments;
    means for determining a plurality of correction factors related to each of said segments;
    means for adjusting a correction factor for a segment identified as having a maximum error; and
    means for repeating said determining and adjusting steps until said error matches a predetermined condition.

11. A system according to claim 10, wherein said predetermined condition is an error threshold.

12. A system according to claim 10, wherein said predetermined condition is a failure to increase after a predetermined number of iterations.

13. A system according to claim 10, including means for adjusting one or more of said segments if said predetermined condition is not met.

14. A system according to claim 10, wherein said means for determining said error includes using the following equations:

$$I_e(r,c) = \Sigma \beta_i s_i(S_i(r,c) + L\sigma_i(r,c) + \gamma_i(r,c))$$

$$S_i(r,c) = \begin{cases} 1 & \text{if } (r,c) \text{ is in primary beam} \\ 0 & \text{if } (r,c) \text{ is not in primary beam} \end{cases}$$

$$\sigma_i(r,c) = \begin{cases} 1 & \text{if } (r,c) \text{ is not in primary beam and not under jaws for the } i\text{th segment} \\ 0 & \text{if } (r,c) \text{ is in primary beam or under jaws} \end{cases}$$

$\gamma_i(r,c)$ = scatter contribution from segment i to the point (r,c)
L = % transmission through MLC leaf
$s_i$ = number of monitor units for the ith segment calculated by segmentation algorithm without considering errors
$\beta_i$ = dosimetry correction factor for the ith segment $$E(r,c) = \frac{|I(r,c) - I_e(r,c)|}{I(r,c)}$$

$$Ea_i = \frac{\sum_r \sum_c S_i(r,c) E(r,c)}{\sum_r \sum_c S_i(r,c)}$$

I is the experimental intensity, E (r,c) is an error matrix over all segments, and E is an average error for the segment.

15. A system according to claim 14, said means for determining a plurality of correction factors including means for setting said correction factors to one or more predetermined initial settings.

16. A system according to claim 15, said means for adjusting a plurality of correction factors including means for using the following equation:

$$E_i(r, c) = \frac{S_i(r, c)(I(r, c) - I_e(r, c))}{s_i}$$

$$\beta new_i = \beta old_i + \text{SignMaxAbs}(E_i(r, c)) * \text{Avg}(|E_i(r, c)|).$$

17. A system for dosimetry correction in a radiation therapy device, comprising:

- means for identifying a set of segments, each of said segments defined by a setting of one or more radiation shielding devices;
- means for identifying an associated set of monitor units for each of said segments;
- means for identifying dosimetry errors; and
- means for varying said associated monitor units for at least one of said segments to correct for said dosimetry errors without adjusting said settings of said one or more radiation shielding devices.

18. A system according to claim 17, further including means for varying a setting of said one or more radiation shielding devices if correction of said dosimetry errors by varying said monitor units fails to meet one or more predetermined criteria.

* * * * *